United States Patent [19] [11] 4,356,825
Veth [45] Nov. 2, 1982

[54] METHOD AND SYSTEM FOR MEASURING RATE OF OCCURRENCE OF A PHYSIOLOGICAL PARAMETER

[75] Inventor: George J. Veth, Fairfield, Colo.

[73] Assignee: United States Surgical Corporation, Norwalk, Conn.

[21] Appl. No.: 129,213

[22] Filed: Mar. 11, 1980

Related U.S. Application Data

[60] Division of Ser. No. 935,642, Aug. 21, 1978, which is a continuation of Ser. No. 769,887, Feb. 18, 1977, abandoned.

[51] Int. Cl.³ .............................................. A61B 5/00
[52] U.S. Cl. ................................... 128/630; 128/671; 128/689; 128/721
[58] Field of Search .............................. 128/670–671, 128/630, 687–690, 700, 702–706, 721–724; 364/415, 417, 701–702, 737, 554

[56] References Cited

U.S. PATENT DOCUMENTS

| | | | |
|---|---|---|---|
| 3,871,360 | 3/1975 | Van Horn et al. | 128/671 |
| 4,053,951 | 10/1977 | Hudspeth et al. | 128/671 |
| 4,129,125 | 12/1978 | Lester et al. | 128/671 |
| 4,181,135 | 1/1980 | Andresen et al. | 128/703 |

OTHER PUBLICATIONS

Haisty, W. K. et al., "Discriminant Function Analysis of RR Intervals: An Algorithm for On-Line Arrythmia Diagnosis", Comptr. & Biomed. Resrch. V5#3, Jun. 1972, pp. 247–255.

Osborne, J. J. et al., "Measurement and Monitoring of Acutely Ill Patients by Digital Computer", Surgery, vol. 64, No. 6, pp. 1057–1070, Dec. 1968.

*Primary Examiner*—Kyle L. Howell
*Assistant Examiner*—Francis J. Jaworski
*Attorney, Agent, or Firm*—Fleit & Jacobson

[57] ABSTRACT

A method system for measuring the rate of occurrence of physiological parameters, such as temperature, pulse rate and respiration rate. A method, implemented by a digital processor associated with an electronic measuring system, provides accurate measurements in a short period of time, which measurements are then displayed to the system operator. Automatic indicator signals or alarm signals are produced whenever data is determined to be invalid. The system is entirely self-contained and, upon completion of a measuring cycle, actuation of the appropriate function key, will visually display the valid data to the operator.

14 Claims, 10 Drawing Figures

METHOD AND SYSTEM FOR MEASURING RATE OF OCCURRENCE OF A PHYSIOLOGICAL PARAMETER

This is a divisional application of U.S. Ser. No. 935,642, filed Aug. 21, 1978, which is a continuation application of U.S. Ser. No. 769,887, filed Feb. 18, 1977 now abandoned.

SUBJECT OF THE INVENTION

The present invention relates to a method and system for measuring the rate of occurrence of a physiological parameter. Such a method and system are useful in electronic monitoring and measuring systems employed in hospitals or the like for simultaneously measuring the temperature, pulse rate, and respiration rate of a patient. The measurements are retained in the instrument for visual display to the operator.

BACKGROUND OF THE INVENTION

At the present time there are numerous electromechanical systems for measuring physiological parameters such as temperature, blood pressure, respiration rate, heart rate and any number of other signs of physical condition which should be monitored for proper health care. Because such systems are generally intended to be portable and carried by the operator from patient to patient in a hospital or other health care facility, the systems must necessarily be contained in rather small packages. Also, because time is generally the limiting factor, accuracy is generally sacrificed for speed. When measuring temperature, most systems take several measurements at a relatively early time before the temperature sensor reaches the equilibrium temperature and than attempt to predict the final temperature. Because speed is essential, it is desirable for such temperature predicting systems to utilize only a limited number of readings in order to arrive at a prediction of the final temperature within a reasonable amount of time. When measuring respiration rate, since it has a relatively low rate, only a few exhalations are detected, and then that number is calculated to produce the final result. When measuring the pulse rate, a major problem has long resided in taking enough time to take sufficient readings so as to accurately produce the actual pulse rate. It is noted that it is very easy for the pulse rate to vary in a short period of time. For example, such variations are often the result of anxiety of the patient brought on by the pulse measuring operation itself. Although, in the past, multi-purpose instruments have been proposed for measuring more than one physiological parameter, these instruments have all operated sequentially, i.e., it was necessary for one measurement cycle to be complete before the next measurement could be taken. This, of course, presents the problem discussed above, that is, expending too much time in performing the measurements. Another failure of all previous measuring instruments has been the inability to sense any abnormalities which may occur at the patient/instrument interface. More specifically, if a temperature probe has been moved about in a patient's mouth during a measurement cycle, thereby causing clearly erroneous readings, the prior systems were not able to detect these abnormalities and the bad readings were used in the calculations. Accordingly, it may be seen that, although in the past electronic device and systems have been available for sensing and measuring various physiological parameters of a patient, such devices have all suffered major drawbacks relating to accuracy and speed. These drawbacks are due chiefly to restrictions on the amount of time available to take the measurements and on the integrity of the patient/instrument interfaces.

SUMMARY OF THE INVENTION

It is therefore an object of the present invention to provide a method system for measuring the rate of occurrence of selected physiological parameters.

It is also an object of the present invention to provide a method and system for measuring the rate of occurrence of selected physiological parameters, which method and system employ tolerance limits pertaining to the range of values of data points corresponding to each occurrence of the measured parameters.

It is a further object of the present invention to provide a method and system for measuring the rate of occurrence of selected physiological parameters wherein the number of times the data point falls within tolerance limits is computed, and is compared with a predetermined number to determine validity of measurement of the physiological parameters.

It is a still further object of the present invention to provide a method and system for measuring the rate of occurrence of physiological parameters, wherein an average of all data points falling within tolerance limits is computed, and the computed average is compared to a previous average to determine whether the difference therebetween is within preselected limits.

The apparatus according to the present invention achieves the above objects, as well as others, by utilizing an essentially digital system for processing the signals which have been produced by the appropriate sensors. In this digital system, a digital processing unit performs the desired temperature anticipation function by using a well-known curve-fitting technique. This curve-fitting technique has not been employed in previous monitoring systems because it requires a larger amount of digital processing memory or space than was heretofore available in such systems. Additionally, a novel algorithm is provided for use by the digital processor to determine the actual pulse rate and respiration rate of a patient based upon a minimum number of samples which may contain spurious noise signals. The present invention operates to take all measurement readings simultaneously and calculates all three above-noted physiological parameters within a thirty second time span.

DETAILED DESCRIPTION OF PREFERRED EMBODIMENT

Figure 1:
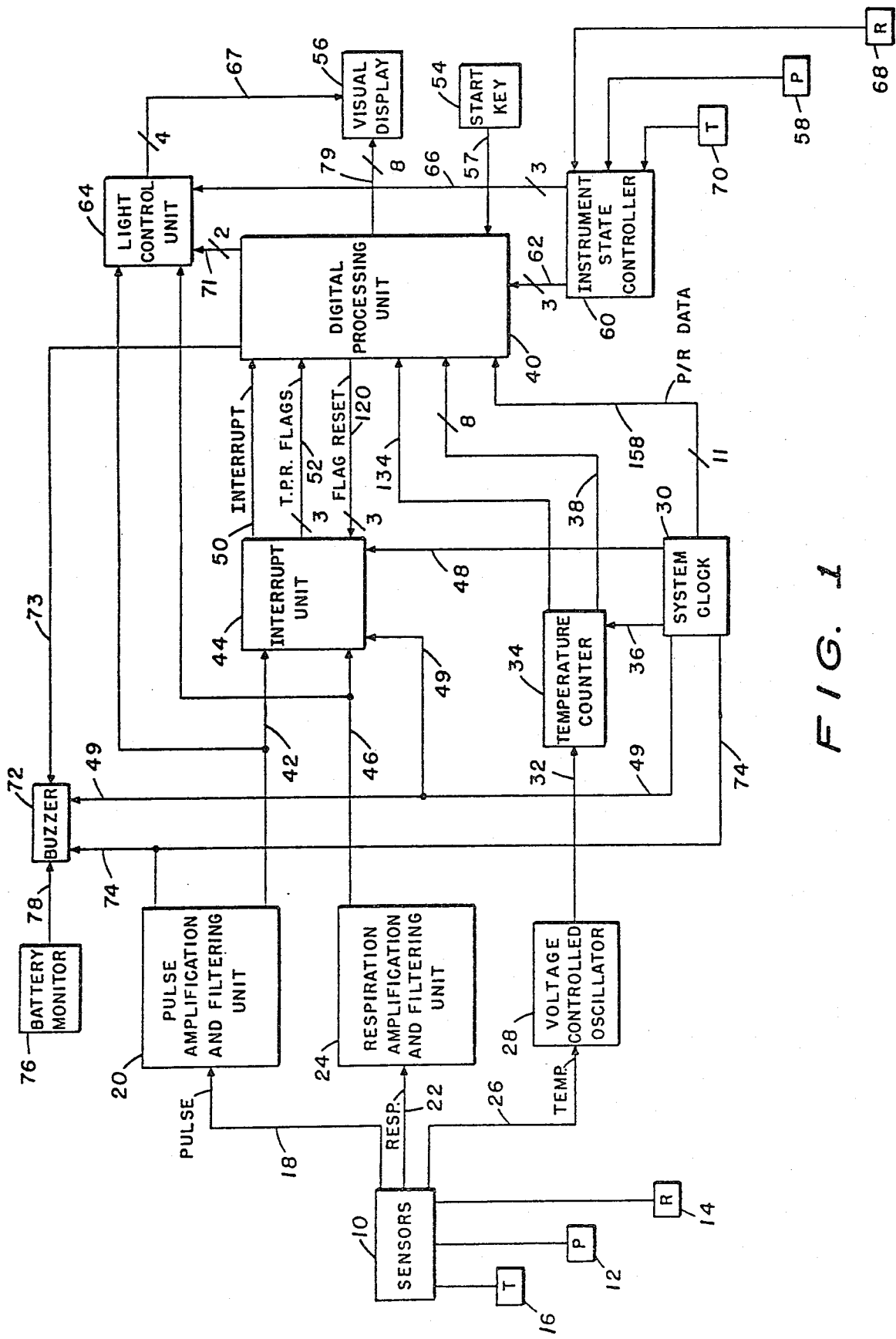
FIG. 1 is a representation of the apparatus of the present invention in block diagram form.

Referring to FIG. 1, the apparatus provided by the present invention is shown represented in block diagram form. Suitable sensors are provided, shown generally at 10, and include: a pulse sensor 12, which may comprise an electro-optical finger-coupling to sense the flow of blood in the flesh of the patient; a respiration sensor 14, which may comprise a highly sensitive thermal element in contact with the respiration exhalation from the patient; and a temperature sensor 16, which may comprise a thermistor for placement in a suitable cavity of the patient. These sensors 12, 14, 16 are then connected to the present invention such that the patient's pulse signal is fed on line 18 to a pulse signal amplification and filtering unit 20, which will be described in more detail later. Similarly, the patient's respiration rate signals are fed on line 22 to a respiration signal amplification and filtering unit 24. The temperature information sensed by the thermistor is fed on line 26 to a voltage controlled oscillator 28. This voltage controlled oscillator 28 may be of a conventional design and is sometimes referred to as a resistance controlled oscillator. The oscillator operates to vary the pulse rate or frequency of its output signal in relation to the change in resistance of the thermistor 16, or the change in voltage drop across the thermistor. As in past systems, the problem in measuring temperature has never been concerned with accurately detecting the variations of temperature but, rather, the problem has been concerned with processing the detected information in an accurate and time-economical manner. The manner in which this problem is solved by the present invention will be subsequently discussed in detail below. Timing for the entire system of the present invention is provided by a system clock 30 which utilizes a conventional oscillator with an adjustable output frequency as a standard. The varying frequency output signal on line 32 from the voltage controlled oscillator 28 is then fed to a digital temperature counter 34 which may comprise conventional binary counters. The temperature counter 34 is gated and reset by the system clock 30 on line 36 and the temperature data, which is represented by eight parallel lines shown generally at 38, is sent to the digital processing unit 40, which will be described in detail below. The digital processing unit 40 of the present invention is intended to process all physiological parameter information as it comes in, and, accordingly, some manner of interrupt system is required to break into the continuously operating digital processing unit 40. This technique of interrupting a continuously operating digital processing system in order to read-in or read-out data is well-known to those familiar with programming and digital processing systems. This technique may be generally described by stating that the processor continuously operates according to some program, e.g., a display program, and when an interrupt signal is presented the program is halted at that position and the specific operation is performed, e.g., new data may be read in, and then the program resumes operation where it was halted. Accordingly, the data signals produced by the pulse amplification and filtering unit 20 are fed on line 42 to an interrupt unit 44 connected to the digital processing unit 40. Similarly, the signals from the respiration signal amplification and filtering unit 24 are fed on line 46 to the same interrupt unit 44. Two system clock signals are also fed to the interrupt unit 44 on lines 48 and 49 in order to properly gate the interrupt signal and read in temperature data into the digital processing unit 40 respectively. When temperature, pulse rate, or respiration rate information are available, the interrupt unit 44 will produce an interrupt signal on line 50 which stops or interrupts the digital processing unit 40 during its continuous operation, indicating that data for use in calculating one of the parameters is being supplied. Of course, not only must the operation be interrupted, but also an indication of what specific parameters are being made available must be given to the digital processor. This is accomplished by the interrupt unit 44 by producing a flag signal on one of three lines 52 which are fed to the digital processor 40. In this way a signal appearing on a particular one of the three lines will indicate that either temperature, pulse rate or respiration rate data is available. In order to commence the pulse and respiration operations of the apparatus of the present invention, a start key is provided at 54 which signals the digital processing unit 40 on line 57 to start the measurement. The actual operation of the system will be described in more detail below. It is noted that, according to the apparatus of the present invention, the start key 54 is not intended to switch the main battery power ON or OFF, but rather this function is performed by interaction of sensors 10 with suitable microswitches located in the instrument housing. Because this type of power-up interlock switching is so conventional, further discussion is not required. In any event, the temperature sensor 16, voltage controlled oscillator 28 and temperature counter 34 are initially enabled so as to begin collecting data to calculate the patient's temperature. However, although the temperature sensor immediately begins to collect data, the digital processing unit 40 will not utilize any data points which are not in excess of ninety-four degrees Fahrenheit, since this temperature is below the expected temperature reading of all but a few patients. Similarly, pulse beats and respiration exhalations are being detected by the sensors 12 and 14 and fed to the interrupt unit 44 so that an interrupt signal and the proper flag signal may be sent to the digital processing unit 40. When it is desired to read out the measured pulse rate, a pulse key 58 is depressed which is connected to the instrument state control unit 60 which signals the digital processing unit 40 on multi-line 62, and also signals a light control unit 64 on multi-line 66. The light control unit 64 produces a signal on multi-line 67 which serves to control the illumination of the appropriate pilot lights, located in visual display unit 56. Each parameter has a key similar to the pulse key 58, such as a respiration key 68 and a temperature key 70. The light control unit 64 is also connected to receive the pulse amplification and filter output signal on line 42, as in the respiration amplification and filter output signal on line 46, so that the appropriate indicator lamp may flash at pulse or respiration rate each time a parameter data point is detected during the measurement period. Upon being enabled by the depression of the pulse key 58 or the respiration key 68, a signal will be placed on the appropriate one of lines 66 from the instrument state control unit 60. In the pulse mode for example, each time the leading edge of a pulse signal is present on line 42, the light corresponding to the pulse measurement will be gated on so as to flash during the measurement period on to provide a visual indication to the operator that the instrument has a proper patient interface and is functioning correctly. A buzzer 72 is provided which will produce an audible signal to the operator when parameter data which can not properly be calculated has been detected. A signal on one line of multi-line 71 to light control unit 64, before and after the measurement time, will cause the pulse or respiration light to remain on continuously. A signal on line 73 from the digital processing unit 40 to the buzzer 72 will indicate this condition. To produce the sound an 800 hertz signal is fed to the buzzer on line 74 from the system clock 30. A battery monitor unit 76 is also provided to detect when the battery output voltage falls below a minimum voltage level. Should this occur a signal is sent from the battery monitor 76 on line 78 to the buzzer 72. In order to permit the operator to differentiate between an erroneous reading indication and a low battery voltage condition, an additional signal is fed to the buzzer 72 from the system clock 30 on line 49. This signal will provide a pulse of 1.28 seconds duration which will gate on and off the 800 hertz signal, thereby causing the buzzer to produce an intermittent sound only when a low battery voltage condition is detected. Two multi-lines 67 and 79 are used to control the visual display 56. Multi-line 67 controls the start, pulse, respiration and temperature lights, and multi-line 79 controls and transmits the calculated parameter data to the visual numeric display.

Figure 2:
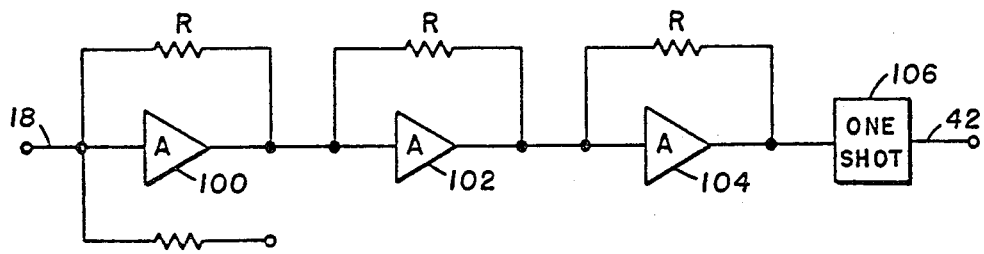
FIG. 2 is a schematic circuit diagram of a typical amplification and filtering unit of FIG. 1, shown in more detail.

Referring now to FIG. 2, the pulse amplification and filtering unit 20 of FIG. 1 is shown in more detail. Because this circuit is essentially the same as the respiration amplification and filtering unit 24, only the one relating to the pulse rate need be shown and discussed in detail. The pulse signal which has been detected by a suitable finger clip or the like is sent on line 18 to a first amplifier stage 100 which serves to increase the amplitude of the detected signal. A major problem in pulse detection has been found to be the wide variations in amplitude among the pulses of different individuals. In other words, a strong pulse has a substantially greater amplitude than the amplitude of a weak pulse beat. The present invention solves this problem by the use of a three stage amplifier utilizing amplifiers 100, 102 and 104, so that any input signal is driven to a maximum gain, thereby performing hard-limiting on the detected pulse signal. In this way all pulse signals of whatever strength will be accomodated. Digital filtering of the first-order is accomplished by the use of a monostable multi-vibrator or non-retriggerable one-shot 106. In this way any noise or spurious signals which may have been detected by a sensor and passed through to the amplifier stage will be ignored unless they recur with a frequency which is less than the pulse-width of the first-order digital filter, i.e., the one-shot 106 of the present embodiment. In the pulse rate filter the one-shot 106 is set to have a output pulse width of 300 millisecond duration. The monostable multivibrator used in the respiration rate signal filter is chosen, however, to have a one second pulse width, although it may be chosen to have any other suitable pulse width. The output signal from the monostable multivibrator 106 appears on line 42 and consists of a 300 millisecond pulse train with each pulse being triggered by the detected patient pulses on line 18.

Figure 3:
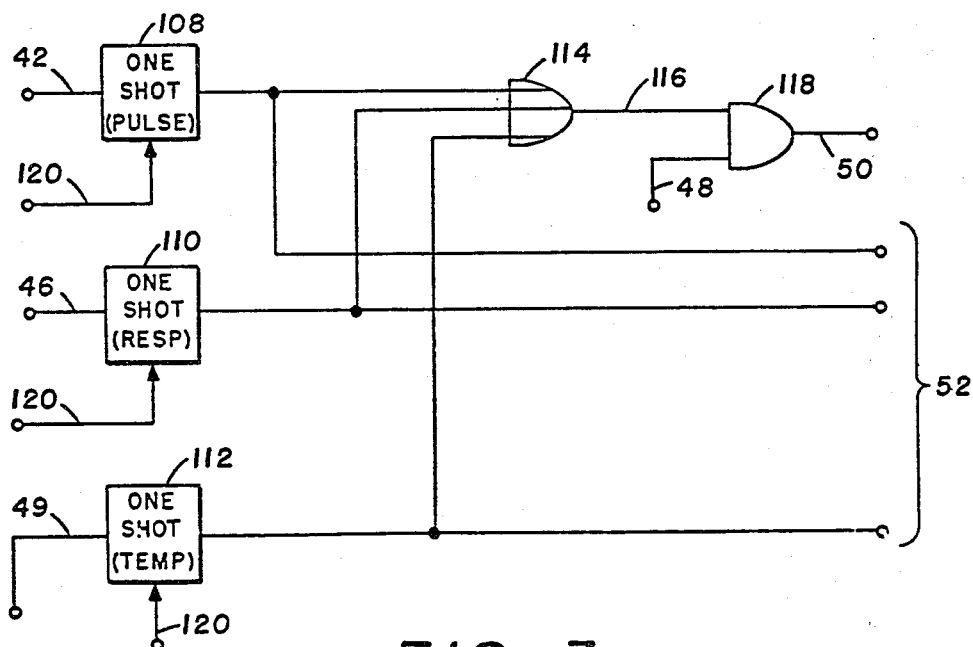
FIG. 3 is a schematic circuit diagram of the interrupt unit of FIG. 1, shown in greater detail.

Looking now at FIG. 3, the interrupt unit, 44 of FIG. 1, is shown in greater detail. The pulse rate signal appearing on line 42, which has a 300 millisecond pulse, for each patient pulse detected, is fed to a monostable multivibrator 108, and the respiration rate signal which has a one second pulse for each patient exhalation detected is fed on line 46 to another monostable multivibrator 110. The temperature strobe is supplied by a signal from the system clock 30 on line 49, which is fed to another monostable multivibrator 112. The output signals from each of these multivibrators will have a pulse width of approximately 20 milliseconds and will be used as flag signals to indicate which particular parameter the interruption is for, and are fed to the digital processing unit 40 on lines 52. These output pulses are also fed to an OR gate device 114. This OR gate 114 serves to determine that at least one parameter has data ready for the digital processing unit 40, and takes three separate random inputs and gates them onto a single line 116. Therefore, upon an occurrence of a pulse from any of the three monostable multivibrators, 108, 110, 112 an output signal will appear on line 116 which is fed to an AND gate device 118. This device has as a second input a signal from the clock on line 48 which serves to develop an interrupt strobe to synchronize the interrupt signal on line 50 which will be fed to the digital processing unit 40. Since each monostable multivibrator 108, 110, 112 is used to flag the specific parameter data being fed to the digital processing unit 40, each one-shot must be immediately reset to insure that the interrupt is recognized only once, since these interrupt signals are random with respect to the system clock. This will be recognized as the conventional "handshaking" operation and reset is accomplished by an appropriate signal from the digital processing unit 40 on one of the three lines shown at 120.

Figure 4:
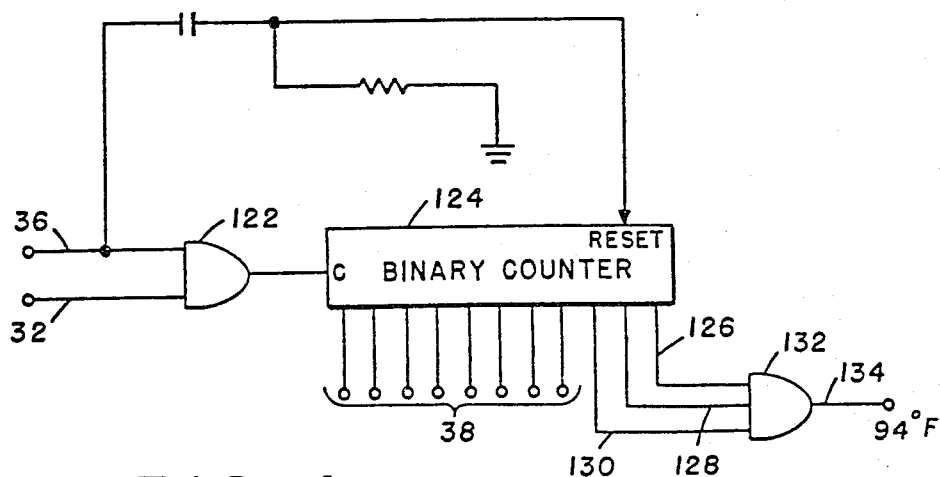
FIG. 4 is a schematic circuit diagram of the temperature counter of FIG. 1, shown in more detail.

Looking now at the operation of the temperature counter 34, as mentioned earlier, a thermistor probe is inserted into the appropriate patient cavity and the resulting variation in resistance used to vary the frequency of a voltage controlled oscillator output signal. The varying frequency counts from the oscillator are then collected by a temperature counter 34 of FIG. 1, which is gated and reset by the system clock on line 36. In operation, the counts corresponding to the temperature sensed are gated into the counter and, upon reaching a predetermined count level a signal corresponding to ninety-four degrees Fahrenheit is produced. Referring then to the temperature counter shown in more detail in FIG. 4, the pulses from the voltage controlled oscillator 28 corresponding to the temperature are fed on line 32 to an AND gate 122 which has as a second input a gate signal appearing on line 36. This signal also resets the binary counter 124 and acts to gate the temperature signal every 0.32 seconds. The gate is opened for a time nominally 0.16 seconds. The pulses are accumulated and upon reaching a level corresponding to ninety-four degrees, this is indicated by a one on the output line of each of the last three stages. By choosing the temperature oscillator base frequency judiciously, the binary counter 124 may be made to have a one on the last three lines 126, 128, and 130 and all zeroes on lines indicated at 38, thereby corresponding to ninety-four degrees. In this way, when all the lines at 38 have a one on them, this corresponds to 106.75 degrees. This signal appears then on line 134 from the AND gate 132.

Because the temperature counter 34 is desired to sense increments of 0.05 degrees, the first stage of the counter will correspond to 0.05, and accordingly the second stage 0.1 and third stage 0.2 and so forth. Turning now to the actual computation of the temperature, it is not desirable from a time stand-point to wait until the entire temperature sensing mechanism has reached an equilibrium temperature, but rather it is desirable to predict or anticipate what the final temperature will ultimately be. In the present embodiment a preselected number of data points indicated by the output signals on parallel lines 38, from the temperature counter 34 are utilized. As discussed in relation to FIG. 4, since ninety-four degrees Fahrenheit is the base temperature, each signal on one of the lines 38 will correspond to some increment above that, with the maximum being 106.75 which is the summation of the eight output lines plus ninety-four. In any event, this preselected number of these temperature values is used by the digital processing unit 40 in such a manner so as to predict the final equilibrium temperature prior to the entire probe and thermistor actually reaching that temperature.

The digital processing unit 40 operates on this data by the use of the mathematical tool known as the least-squares fit in order to anticipate the final temperature. It has been found, experimentally, that the temperature versus time response curve of the temperature sensor utilized in this preferred embodiment most closely approximates a hyperbolic curve. Accordingly, the digital processing unit will then operate on the temperature data on lines 38 in accordance with the least-squares fit rules and attempt to fit the data to a hyperbolic curve. Because curve fitting by use of the least-squares technique is exceedingly well known, the actual steps performed by the digital processing unit 40 in predicting the temperature will now be described.

Figure 5:
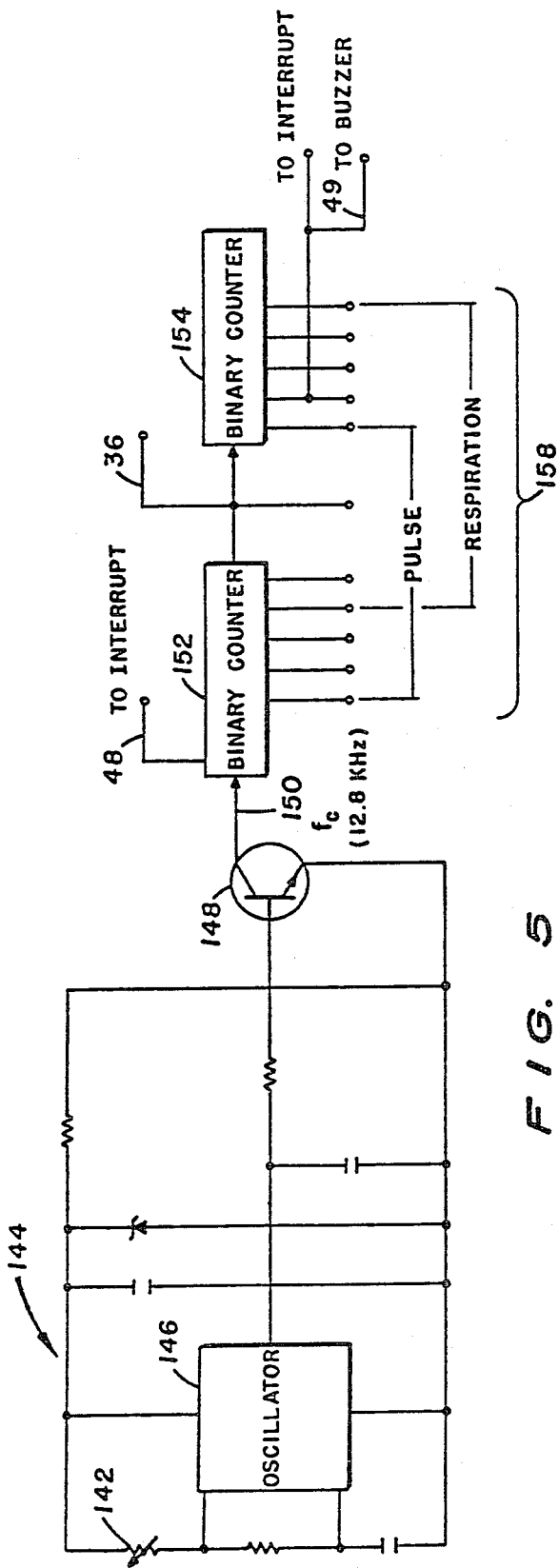
FIG. 5 is a schematic circuit diagram of the system clock of FIG. 1, shown in greater detail.

Referring now to FIG. 5 the system clock oscillator and system clock counter identified only as a system clock at 30 in FIG. 1, are now shown in more detail. A variable resistor 142 controls an oscillator unit shown generally at 144 to produce an output at 12.8 Khz. The heart of this oscillator is a commercially available oscillator microcircuit shown at 146. The output signal from the oscillator is then fed to the base of a transistor 148 where the signal is buffered by the transistor. The output signal on line 150 is the desired frequency rate of 12.8 kilohertz. This fixed frequency signal is fed to the counter portion of the clock which comprises two binary counters 152 and 154. The clock signal on line 150 is fed into the first binary counter 152, having outputs which correspond to the powers of two as in conventional digital circuits. The first binary counter 152 then overflows on line 36 into the second binary counter 154. The signal corresponding to the overflow of the first register is fed back on line 36 to the AND gate 122 of the temperature counter shown in FIG. 4, which is used to gate the temperature signal from the voltage controlled oscillator. The second binary counter 154 accumulates the counts also in the conventional manner. One of the counter portions of binary counter 154 is utilized on line 49 to gate on the buzzer shown at 72 in FIG. 1. This same signal appearing on line 49 is also fed to the interrupt unit 44 of FIG. 1, and there acts to trigger the one shot 112 shown in FIG. 3 to provide a strobe which causes the digital processing unit 40 to measure temperature and to trigger the OR gate 114 to provide the interrupt signal for the digital processing unit as discussed above. These output signals from the binary counters 152 and 154 are then used by the digital processing unit 40 as data points corresponding to pulse and respiration and are shown generally at lines 158 in FIG. 5, and are also shown as an eleven parallel line input at 158 in FIG. 1. These pulses on lines 158 then are the pulse and respiration data from which the digital processor can calculate the patient's pulse and respiration rate as detected by the sensors. The digital processing unit uses the numbers, or more correctly the bit patterns, in the binary counters 152, 154, which correspond to some system-based time, in conjunction with the interrupt signal to measure the real time which occurs between the successive pulse or respiration interrupt signals. The specific pulse and respiration lines of the group of lines at 158 from the binary counters 152 and 154 are chosen as shown because the respiration and pulse rates naturally occur at different frequencies.

Figure 6:
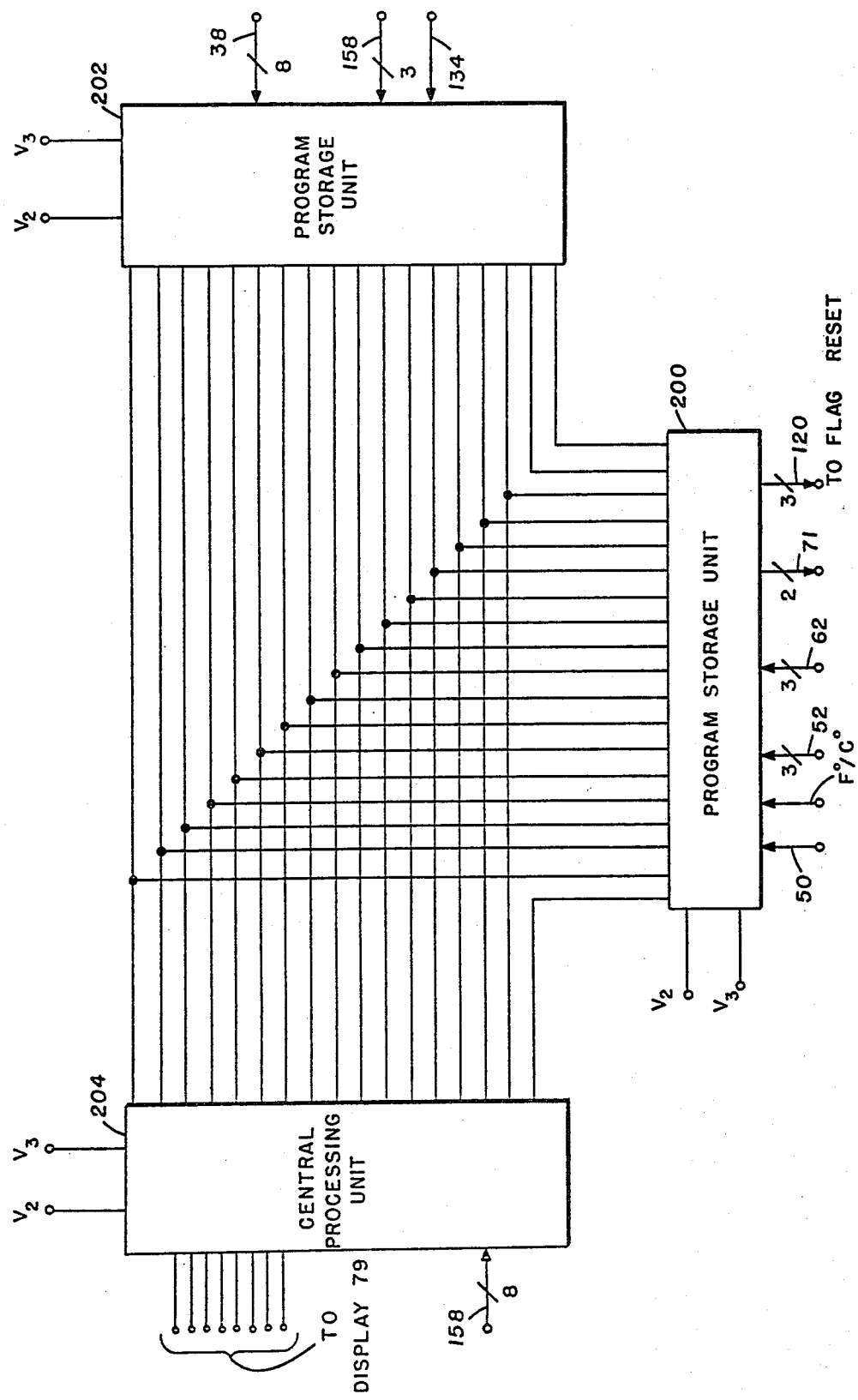
FIG. 6 is a representation of the digital processing unit of FIG. 1, shown in block diagram form.

Referring now to FIG. 6, the digital processing unit 40 of FIG. 1 is shown in more detail. The digital processing unit may be implemented by commercially available microprocessor sections which generally have approximately 40 pins or input/output connections. For example, a suitable microprocessor might be the model F8 produced by the Mostek Corporation or Fairchild Corporation. In the present embodiment of the digital processing unit, first and second microprocessor sections 200 and 202 may be utilized as program storage units. These units will contain the particular algorithms to be utilized in calculating the temperature and pulse and respiration rates. Similarly, a central processing unit 204 is required to perform the actual mathematical operations and, as is well known, is the heart of all digital processing systems. As may be seen from FIG. 6, these three units are interconnected by sixteen common lines on which the three sub-units can communicate. All necessary data points required to permit the processing unit to calculate the temperature, pulse rate and respiration rate are fed into the digital processing unit as seen in FIG. 1. More specifically, the temperature data which is produced by the temperature counter 34 of FIG. 1 is provided via the eight parallel lines shown at 38 to an input/output section of the program storage unit 202. The pulse and respiration data, which consists of pulse data from the counter of the system clock, are provided to an input/output section of program storage unit 202 and the input/output section of the central processing unit 204 via the multiple parallel lines 158. Because the program storage unit 200 has been programmed to perform the specific algorithms of the present invention, these algorithms will now be discussed. Of course, as mentioned above, in order to calculate the temperature, the algorithm utilized relates to the least squares fit of a hyperbolic curve, and accordingly it is not necessary to describe this well-known procedure.

Figure 7:
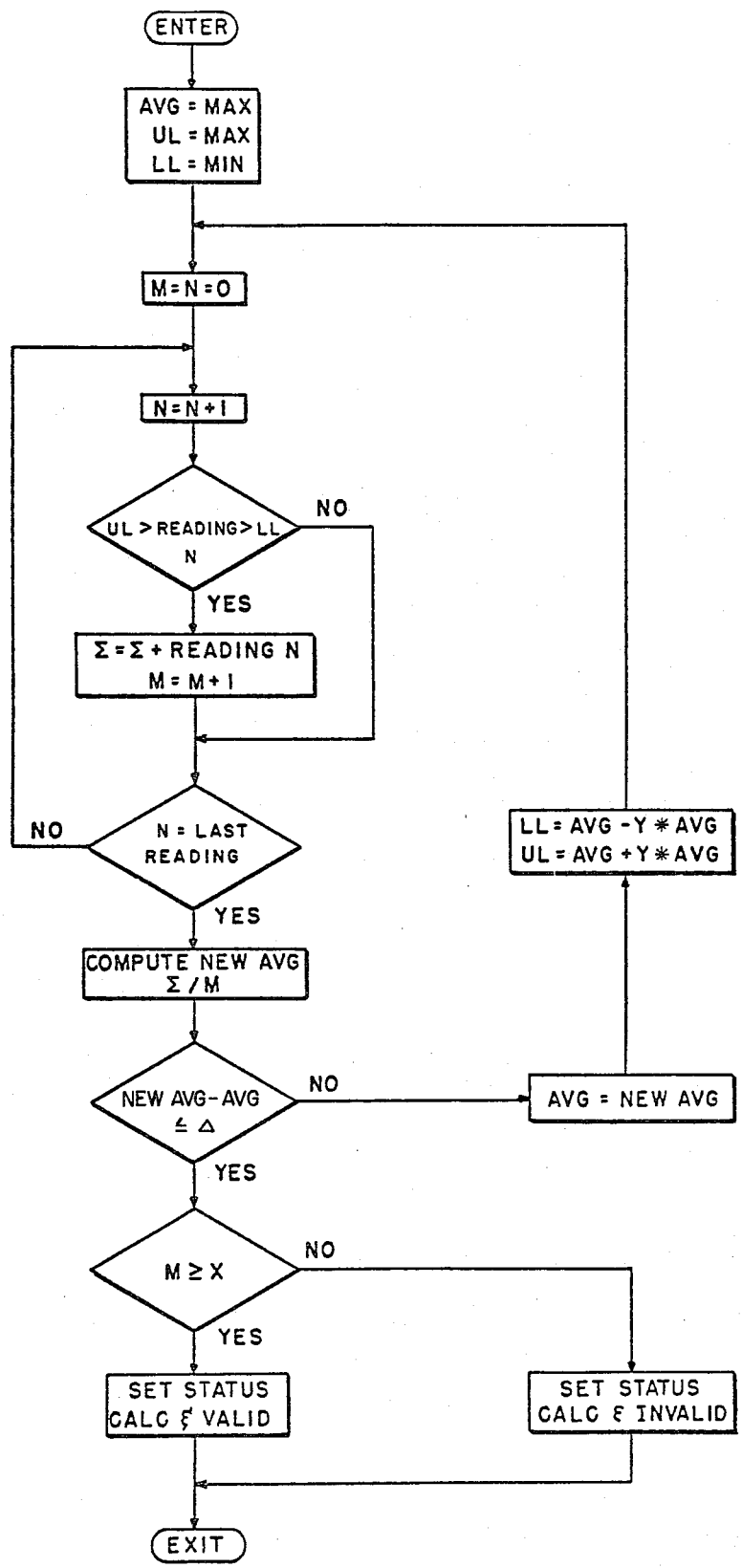
FIG. 7 is a flow chart in conventional notation showing the steps of the novel algorithm utilized by the digital processor in determining pulse and respiration rates.

Turning then to FIG. 7, the algorithm for calculating the pulse rate and respiration rate is shown. Because this algorithm contains steps utilizing certain constants, by changing these constants, it is possible to use the same algorithm for both the pulse rate and the respiration rate calculations. The present algorithm shown in FIG. 7 determines whether or not a valid average exists when more than a certain number of data points are within a tolerance of an average. If there are as many as or more than this certain number of data points within the plus or minus tolerance of the average, then that average is certified as valid, and, if sufficient points are not within the tolerance range, the average is certified as invalid. If the average is certified as invalid a signal is sent from the digital processing unit on line 73 to the buzzer 72 to alert the operator that incorrect data has been supplied to the instrument. FIG. 7 shows a flow chart corresponding to this algorithm and, as may be seen from this flow chart, which is done in the conventional format, the steps of the present algorithm beginning at the first block are: (1) set the average equal to a minimum or maximum value, set the upper limit to a maximum value and the lower limit to a minimum value. As mentioned above, it is necessary to generate new averages, and hence the next step (2) in the present algorithm is to generate a new average utilizing only data points which are less than the upper limit and greater than the lower limit. The next step (3) then is to (3) compare the previous average with the new average and, if the two values are within an allowed variance, then the next step (4) is to continue and check the number of pulse data points M which were used to generate this average. If this number of data points M is equal to or greater than a predetermined value X which, as mentioned, is the certain number of data points, then the average is labelled valid. However, if this number M is less than the predetermined number X of data points, the average is labelled invalid, and an error signal is sounded.

Referring back to the previous step (3), if the variance between the previous average and the new average is not within the allowed variance, then (5) the old average is replaced with the new average, new upper and lower limits are calculated from the new average, and the loop is reentered at step (2). The steps are again repeated until an average is achieved wherein the new average is within plus-or-minus the allowed variance of the old average.

In regard to the flow chart of the present algorithm, the abbreviations utilized in the flow chart are as follows:

READING N=value of pulse (respiration) data point N
N=a running count of the number of pulse (respiration) data points examined
M=a running count of the number of valid pulse (respiration) data points
X=required number of valid pulse (respiration) data points
Y=a percentage (an arbitrary, predetermined constant used to determine distance of upper limit and lower limit from average) used to compute upper and lower limits based on the value of the average
UL=upper limit
LL=lower limit
$\Delta$=allowed variance.

As mentioned, this same algorithm may be used in calculating the respiration rate and, of course, since the respiration rate is significantly lower than the pulse rate, a lesser number of required data points (X) is used to calculate the respiration rate. Moreover, when calculating pulse rate, the amount of variance between old and new averages, indicated as delta in the flow chart, will be adjusted to a value different from that for the pulse algorithm. Specifically, the pulse rate measurement can tolerate only a 25% variance in averages (i.e., delta will equal 25%) whereas, in the respiration rate measurement, since the respiration rate has a tendency to be less constant than the pulse rate, a larger variance in averages is used (delta equals 50%) in the algorithm.

Figure 8:
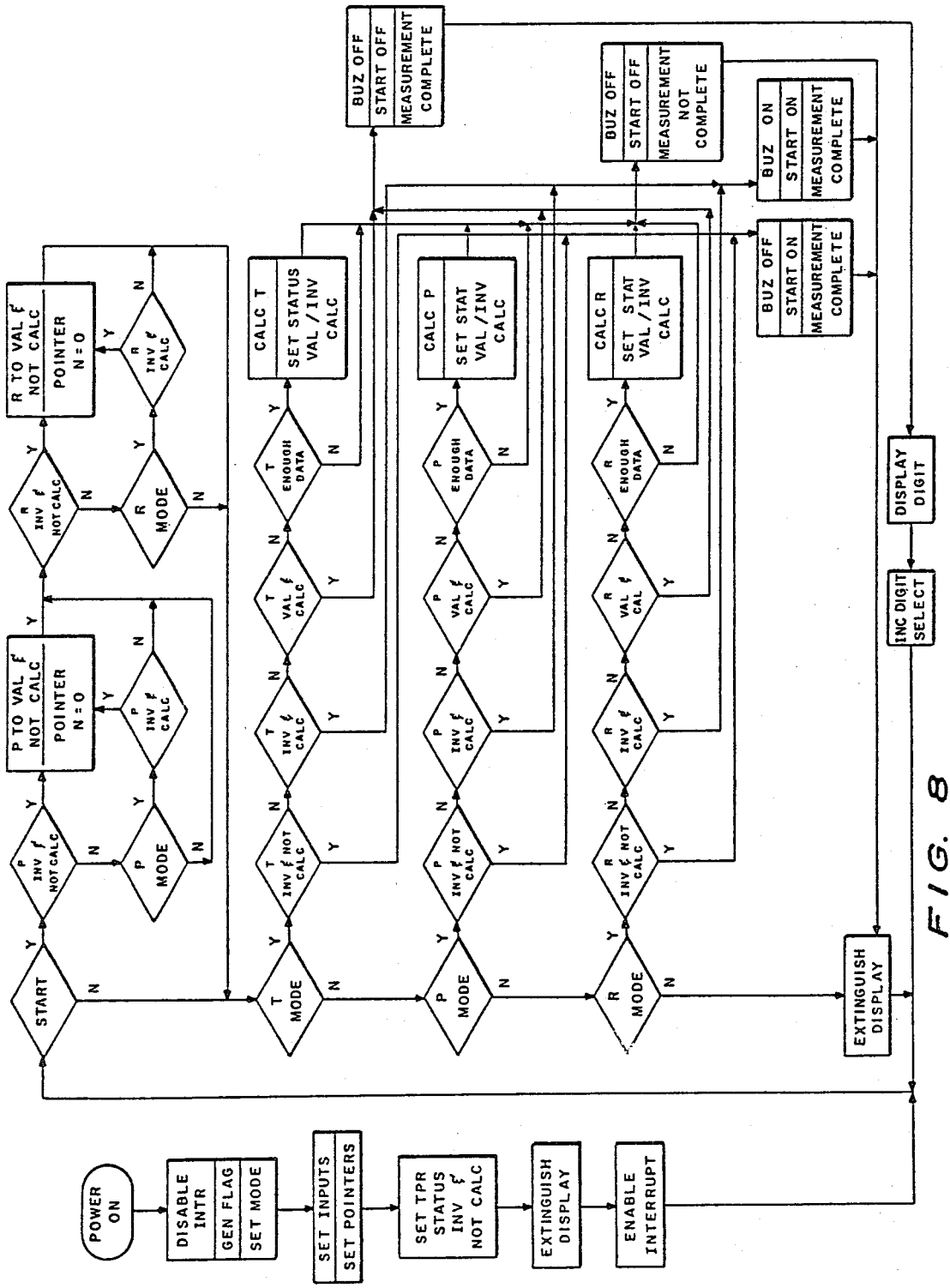
FIG. 8 is a flow chart in conventional notation showing the algorithm of the display program which is processed by the digital processor.

Looking now at FIG. 8, a flow chart is shown using the conventional format. As discussed earlier, the digital processing unit of the present invention is intended to operate continuously in some predetermined mode in which it awaits data to be supplied it. More particularly, the digital processor continuously operates in some mode and when an interrupt signal appears, on line 50, it stops the continuous program at that particular instant and than looks to see what flag is raised to determine what manner of data is being supplied, i.e., temperature, pulse or respiration. This data is then accepted and the continuous program mode is resumed. When the proper amount of data has been input to the processing unit the continuous program mode will automatically calculate the appropriate measurement, as may be seen from the "calculate" block of FIG. 8. FIG. 8 then is a conventional flow chart of the continuous mode of the digital processing unit of the present invention. More particularly the digital processor is caused to continuously operate in a display type mode where it is constantly attempting to display some operational condition or some calculated parameters. Looking at the actual information contained in the blocks of the flow chart of FIG. 8 it may be seen that the display loop is attempting to display some sort of validly calculated data, either temperature, respiration or pulse, and that it continuously attempts to display such data.

Figure 9:
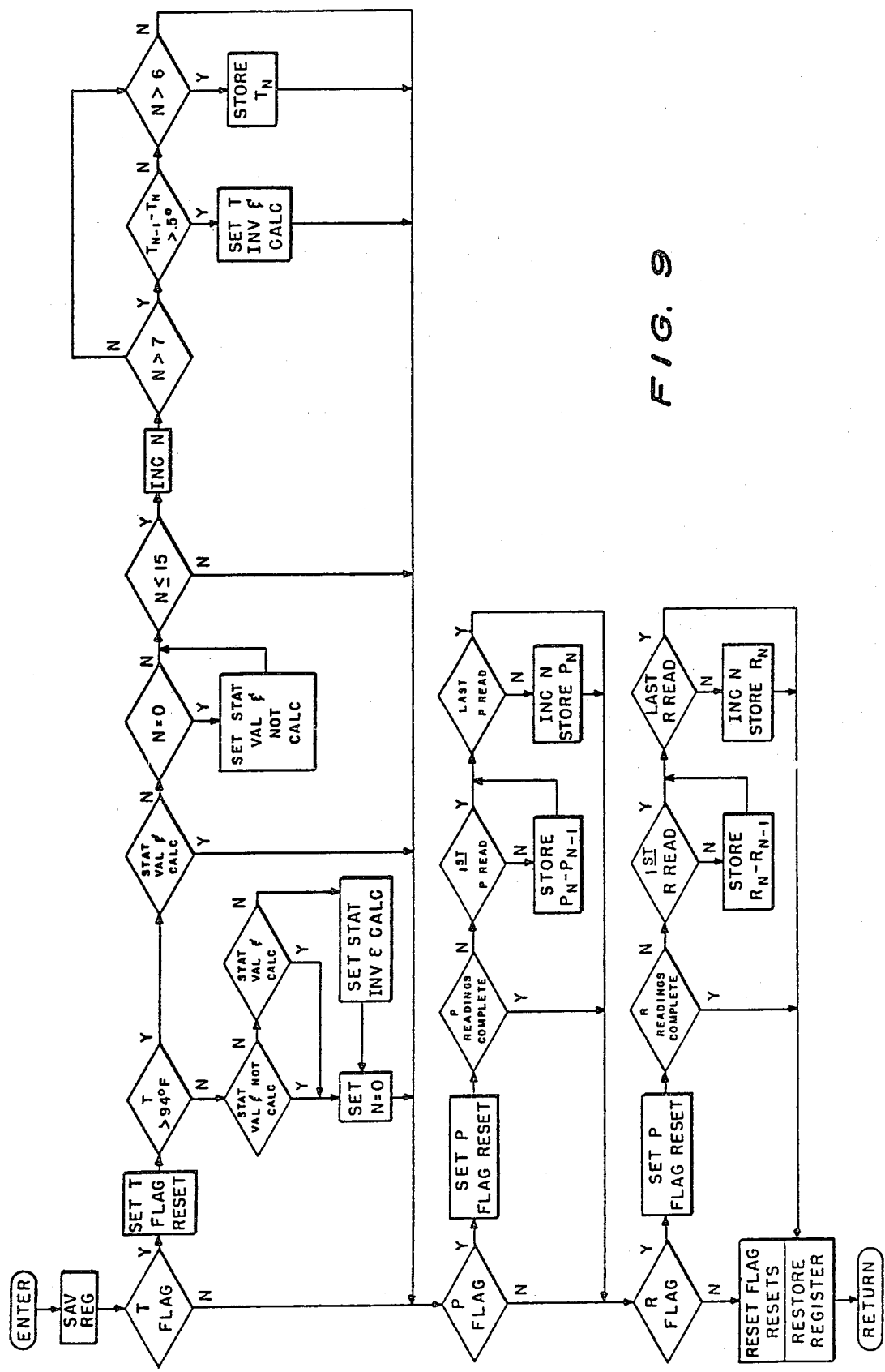
FIG. 9 is a flow chart in conventional notation showing the algorithm of the interrupt routine which is utilized in the digital processing unit.

FIG. 9 is a conventional format flow chart showing the interrupt flow chart of the present invention. As may be seen, the decisional blocks relating to the particular flags are present and are the first that are interrogated. It will be noted that in looking at the statements made in the decisional blocks or the instructional blocks of the interrupt program of FIG. 9, that many of the inputs and outputs generated and utilized in the preceeding schematic diagrams are originated in the decisional block and instructional blocks. For example, it will be noticed that if a parameter flag is found to be present that the very next step to be taken is to reset the flag. This was shown and discussed for example in relation to resetting the interrupt unit 44 by signals appearing on one of the three parallel lines 120 of FIG. 1. Turning then to the particular interrupt routine which relates to the temperature measurement operation, it will be seen that the first decision that is to be made is whether or not the temperature is above ninety-four degrees. Should this not be the case the information will not be permitted to be entered into the digital processing unit so that such data is never utilized in the calculating the temperature. A set number of initial data points after the temperature is above ninety-four degrees Fahrenheit are also neglected. Once however the ninety-four degree temperature has been reached by the sensing unit, and this initial number of data points have been rejected, the interrupt routine will, of course permit the number of frequency counts corresponding to the voltage control oscillator output signal to be entered into the digital processing unit for calculating the temperature in accordance with the least-squares rule. It has been found that approximately nine readings are necessary to accurately predict the final temperature. Accordingly, it may be seen from the portion of the interrupt routine corresponding to temperature, that nine readings are in fact taken and entered into the digital processing unit 40. It has been found that a period of time between the successive temperature measurements may be approximately 1.25 seconds and in this way a sufficient number of valid data points may be taken to accurately predict the final temperature.

Figure 10:
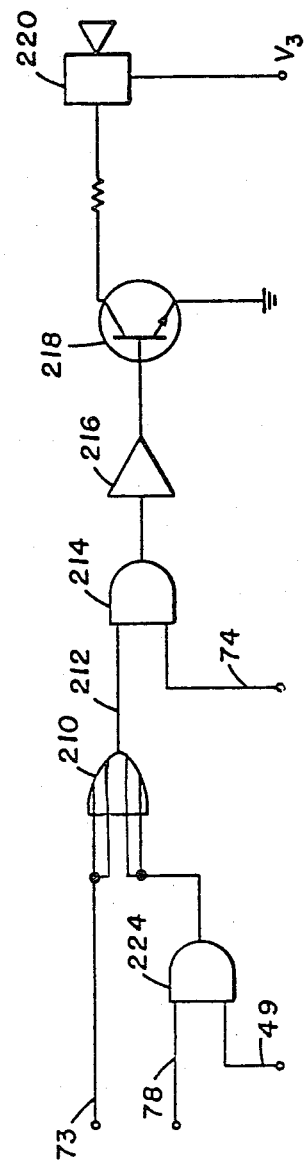
FIG. 10 is a schematic circuit diagram of the buzzer unit of FIG. 1, shown in more detail.

Upon examining the flag after the occurrence of an interrupt signal, should it be found that a pulse flag has been raised, in same manner corresponding to the discussion of the temperature cycle, the first instruction is to reset the pulse interrupt unit. The remaining portion of the pulse interrupt routine then serves only to permit the required number of data points to be input to the digital processing unit. It has been found through experimentation, that sixteen readings of the intervals between the detected pulses are sufficient to accurately calculate the pulse rate by the use of the algorithm shown in FIG. 7. Accordingly, the duty of the pulse interrupt group is merely to assure that sixteen pulse readings are in fact taken. Similarly the respiration group operates in the same way and upon seeing a respiration flag the flag is reset and the number of respiration rate readings is permitted to be entered into the digital processing unit. As mentioned previously, because the respiration rate is less than the pulse rate a fewer number of readings are taken. Therefore, it has been found that only four readings of the intervals between successive respirations need to be utilized in the algorithm of FIG. 7 to accurately calculate the patients respiration rate. Looking now at FIG. 10, the other unit 72 of FIG. 1 is shown in more detail. The buzzer unit operates to produce a continuous output when an erronous or invalid calculation has been performed. Such condition is indicated by a signal appearing on line 73 from the digital processing unit such signal is fed to a OR gate. Upon such signal appearing at the OR gate 210 an output will appear at line 212, which output is fed to an AND gate 214. In addition a 800 hertz signal from the system clock appearing on line 74. Gating these two signals together in the AND gate 214 produces a signal in the audio range suitable for alerting the operator. Such signal is passed through an inverting amplifier 216 and a buffering amplifier 218, shown as a transistor, and then fed from the transistor 218 to a miniature speaker shown at 220 which is provided with a suitable energizing voltage V3 such that an audible tone is produced to the operator. In the case that the battery monitor 76 detects a low battery voltage condition, an output signal is produced on line 78 which is fed through a second AND gate 224, also input to AND gate 224 is a pulse signal from the system clock appearing on line 49 which occurs every 1.25 seconds. Accordingly, the output from AND gate 224 will be a pulse signal which is fed to OR gate 210, from this point the operation is the same as if the alarm signal were indicated on line 73 except that the speaker 220 will be caused to modulate or pulse the 800 hertz signal, thereby producing a beeping tone rather than a continuous buzzing tone.

It is of course understood that the above description of the preferred embodiment is given by way of example only and that various other components could be utilized to achieve the apparatus taught by the present invention. For example, the digital processing unit need not be built up of three separate micro processor circuits but may be made up of only one larger micro processor ciruict or in fact several smaller more discrete components.

What is claimed is:

1. A method for measuring a physiological parameter of a patient in a rapid manner by converting successive measurements of the physiological parameter into a final measurement value thereof, comprising the steps of:
   (a) detecting successive occurrences of the physiological parameter;
   (b) producing, in response to said successive occurrences of said physiological parameter, data points representing values of said physiological parameter;
   (c) comparing each of said data points with a predetermined range to determine those data points having a value falling within said predetermined range, and determining the number of said data points having a value falling within said predetermined range;
   (d) computing an average of all said data points having a value falling within said pre-determined range;
   (e) determining if said computed average falls outside of said predetermined tolerance limits, and if so, substituting said computed average as a new average; and
   (f) determining if said computed average falls within said predetermined tolerance limits, and if so, comparing the determined number of said data points having a value within said predetermined range with a pre-selected number, declaring the computed average to be an invalid calculation if the determined number of date points is less than said pre-selected number, and declaring the computed average to be a valid calculation if the determined number of date points is greater than said pre-selected number;
   whereby to rapidly obtain for display a valid final measurement value of the physiological parameter from said date points.

2. The method of claim 1 wherein the step of detecting successive occurrences of the physiological parameter comprises the step of detecting the pulse beat of the patient.

3. The method of claim 2 further including the step of producing an indication that the computed average is an invalid calculation.

4. The method of claim 2 further including the step of displaying the computed average which has been declared a valid calculation.

5. The method of claim 1 wherein the step of detecting successive occurrences of the physiological parameter comprises the step of detecting the occurrence of a respiration of the patient.

6. The method of claim 5 further including the step of producing an indication that the computed average is an invalid calculation.

7. The method of claim 5 further including the step of displaying the computed average which has been declared a valid calculation.

8. A system for measuring a physiological parameter of a patient in a rapid manner by converting successive measurements of the physiological parameter into a final measurement value thereof, comprising:
   means for detecting successive occurrences of the physiological parameter;
   means for producing, in response to said successive occurrences of said physiological parameter, date points representing values of said physiological parameter;
   means for comparing each of said data points with a predetermined range to determine those data points having a value falling within said predetermined range, and determining the number of said data points having a value falling within said predetermined range;

means for computing an average of all said date points having a value falling within said predetermined range;

means for determining whether said computed average falls within predetermined tolerance limits;

means responsive to said computed average falling outside said predetermined tolerance limits for substituting said computed average as a new average; and means responsive to said computed average falling within said predetermined tolerance limits for comparing the determined number of said data points having a value within said predetermined range with a preselected number, and for declaring the computed average to be an invalid calculation if the determined number of data points is less than said preselected number, and for declaring the computed average to be a valid calculation if the determined number of data points is greater than said preselected number; whereby to rapidly obtain for display a valid final measurement value of the physiological parameter from said data points.

9. The system of claim 8, wherein said means for detecting successive occurrences of the physiological parameter comprises means for detecting the pulse beat of the patient.

10. The system of claim 9, further including means for producing an indication that the computed average is an invalid calculation.

11. The system of claim 9, further including means for displaying the computed average which has been declared a valid calculation.

12. The system of claim 8, wherein said means for detecting successive occurrences of the physiological parameter comprises means for detecting the occurrence of a respiration of the patient.

13. The system of claim 12, further including means for producing an indication that the computed average is an invalid calculation.

14. The system of claim 12, further including means for displaying the computed average which has been declared a valid calculation.

* * * * *